(12) United States Patent
Langner

(10) Patent No.: US 12,678,108 B2
(45) Date of Patent: Jul. 14, 2026

(54) ACQUISITION OF PROTON COMPUTED TOMOGRAPHY IMAGES

(71) Applicant: Rhode Island Hospital, Providence, RI (US)

(72) Inventor: Ulrich Langner, Upton, MA (US)

(73) Assignee: Rhode Island Hospital, Providence, RI (US)

( * ) Notice: Subject to any disclaimer, the term of this patent is extended or adjusted under 35 U.S.C. 154(b) by 550 days.

(21) Appl. No.: 18/147,455

(22) Filed: Dec. 28, 2022

(65) Prior Publication Data

US 2023/0210476 A1 Jul. 6, 2023

Related U.S. Application Data

(60) Provisional application No. 63/296,749, filed on Jan. 5, 2022.

(51) Int. Cl.
| | |
|---|---|
| *A61B 6/03* | (2006.01) |
| *A61B 6/40* | (2024.01) |
| *A61B 6/42* | (2024.01) |
| *G01N 23/046* | (2018.01) |

(52) U.S. Cl.
CPC ............ *A61B 6/032* (2013.01); *A61B 6/4071* (2013.01); *A61B 6/4258* (2013.01); *A61B 6/4291* (2013.01); *G01N 23/046* (2013.01); *A61B 6/037* (2013.01)

(58) Field of Classification Search
None
See application file for complete search history.

(56) References Cited

U.S. PATENT DOCUMENTS

| | | | |
|---|---|---|---|
| 2006/0145088 A1* | 7/2006 | Ma ........................ | H05H 15/00 250/396 ML |
| 2011/0220794 A1* | 9/2011 | Censor ................. | A61B 6/4258 250/307 |
| 2017/0150934 A1* | 6/2017 | Bennett ................ | A61N 5/1077 |
| 2019/0108968 A1* | 4/2019 | Papeer ................... | G21K 5/04 |

OTHER PUBLICATIONS

Penfold , et al., "Techniques in Iterative Proton CT Image Reconstruction", Sensing and Imaging, vol. 16, No. 19, 2015, pp. 1-21.
Poludniowski , et al., "Proton Radiography and Tomography with Application to Proton Therapy", The British Journal of Radiology, vol. 88, No. 1053, 2015, pp. 1-14.
Saraya, et al., "Study of Spatial Resolution of Proton Computed Tomography Using aSilicon Strip Detector", Nuclear Instruments and Methods in Physics Research, vol. 735, 2014, pp. 485-489.
Takabe, et al., "Development of Simple Proton CT System with Novel Correction Methods of Proton Scattering", Nuclear Inst. and Methods in Physics Research, vol. 924, 2019, pp. 332-338.

* cited by examiner

*Primary Examiner* — James Choi
(74) *Attorney, Agent, or Firm* — Adler Pollock & Sheehan P.C.

(57) ABSTRACT

A method includes providing a proton computed tomography (CT) scanner, and measuring sigma with a scintillator screen at an exit beam for each pencil beam scanned across an object for each gantry angle necessary to determine a total energy loss as the beam traverses an object of unknown thickness or material.

6 Claims, 3 Drawing Sheets

*500*

Normalized (at entrance) Bragg Curves for Various Proton Incident Energies

*600* *602*

*700*

ACQUISITION OF PROTON COMPUTED TOMOGRAPHY IMAGES

CROSS REFERENCE TO RELATED APPLICATIONS

This application claims benefit from U.S. Provisional Patent Application Ser. No. 63/296,749, filed Jan. 5, 2022, which is incorporated by reference in its entirety.

STATEMENT REGARDING GOVERNMENT INTEREST

None.

BACKGROUND OF THE INVENTION

The present invention relates generally to proton computed tomograpy (CT), and specifically to acquisition of proton computed tomograpy (CT) images.

In general, proton therapy has attracted attention because a proton deposits most of its energy just before it stops (the Bragg peak), and it is possible to concentrate the proton dose on a tumor. Typical treatment planning for proton therapy is based on photon CT images, whose pixel values are determined by atomic number and density of a phantom.

Currently, no commercially-available device exist for acquiring proton CT scans. Devices that are used in research focus on measuring a Bragg peak position of a proton beam after exiting a subject. In order to scale these devices for human use, they need to use a proton beam energy of ~250 MeV, resulting in a Bragg peak depth in water at ~39 cm, in order to be able to traverse a subject and not stop inside the subject. Conversely, a detector must have a water equivalent thickness to stop the beam even if it passed only through air. These devices are typically large and heavy, making it difficult to rotate it around patients.

SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In general, in one aspect, the invention a method including providing a proton computed tomography (CT) scanner, and measuring sigma with a scintillator screen at an exit beam for each pencil beam scanned across an object for each gantry angle necessary to determine a total energy loss as the beam traverses an object of unknown thickness or material.

In another aspect, the invention features a method including providing a proton computed tomography (CT) scanner, for a proton pencil beam of known energy entering an object, measuring a sigma at a beam exit with a scintillator screen, modeling sigma for proton beams traversing objects of different thickness and composition with a Monte Carlo model, establishing correlations with the exiting energy of the beam, scanning the beam over the object in a plane and over 360 degrees around the object, measuring the sigma of each pencil beam at the exit, and determining a total energy loss for each beam path.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

These and other features, aspects, and advantages of the present invention will become better understood with reference to the following description, appended claims, and accompanying drawings where:

DETAILED DESCRIPTION

Figure 1:
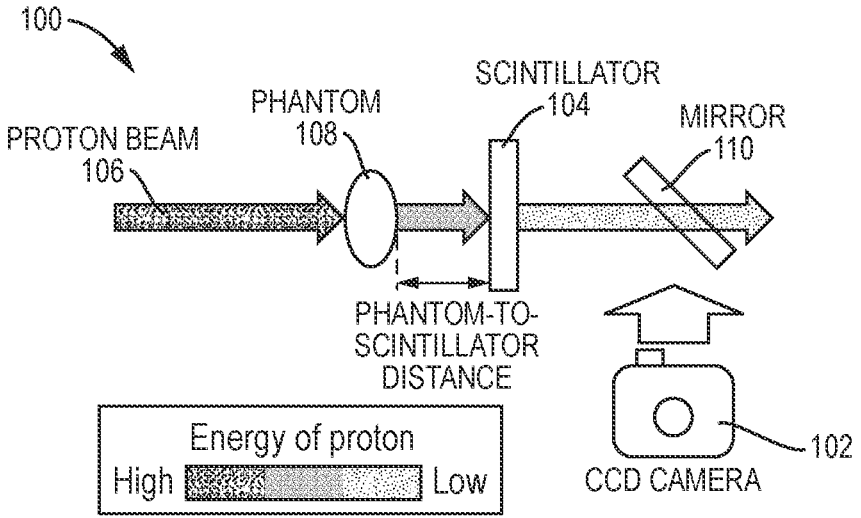
FIG. 1 illustrates an exemplary proton computed tomograpy (CT) system.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

FIG. 1 illustrates an exemplary proton computed tomograpy (CT) system 100. As those of skill in this art recognize, other experimental setups may be employed. In the system 100, a CCD camera 102 (e.g., BITRAN, BU66-EM) is coupled with a C-mount F-1.4 lens (e.g., LM16JC1MS, Kowa Optical Products) and a Gd2O2 S:Tb scintillator sheet 104 (e.g., FUJI Film X-ray intensifying screen HR-16, 160×210 mm2). A 200 MeV beam 106 requires a thicker scintillator than a 70 MeV beam because the proton stopping power becomes smaller when the incident energy becomes larger. Therefore the scintillator sheet 104 has a thickness of 0.75 mm for 200 MeV protons and 0.25 mm for 70 MeV protons. After passing through a phantom 108, the decelerated proton deposits a portion of its energy within the scintillator 104. Here, a mirror 110 is set in order to prevent the camera 102 from radiation damage.

Figure 2:
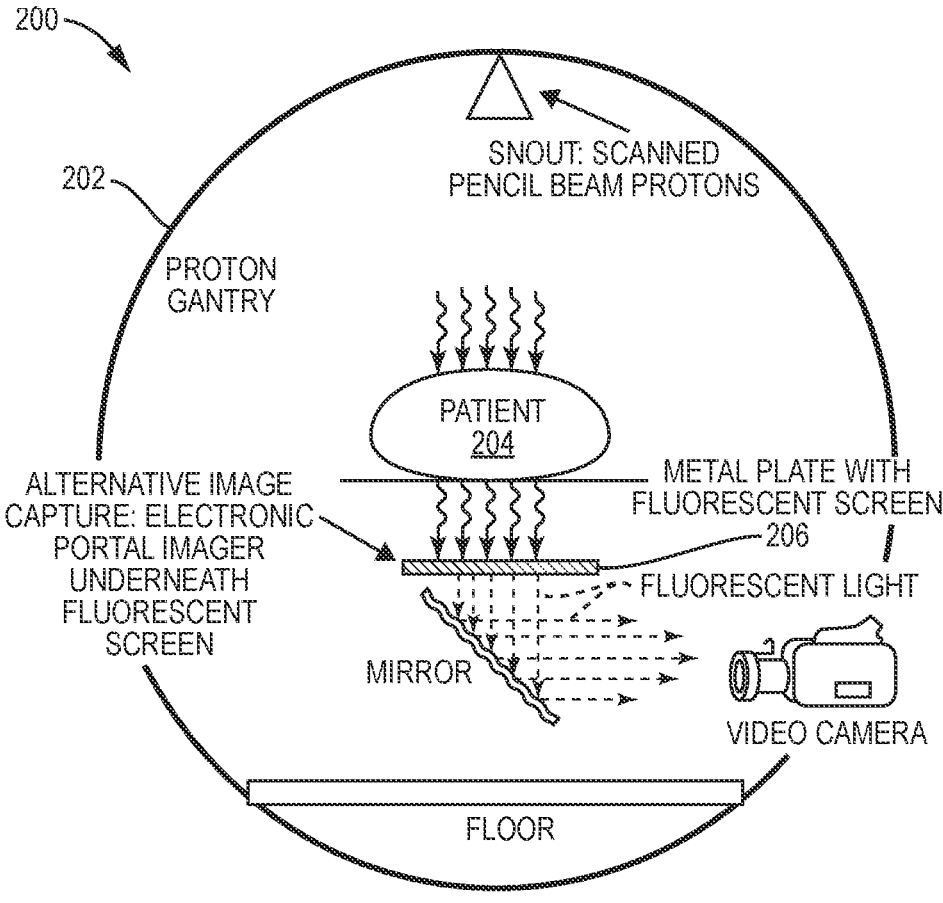
FIG. 2 illustrates an exemplary Proton CT acquisition system in accordance with the present invention.

FIG. 2 illustrates an exemplary Proton CT acquisition system 200 in accordance with the present invention, wherein protons from a gantry 202 go through a patient 204 and are detected by a scintillator screen 206 where a profile is measured.

In the photon CT scanner 200, a grid is used in front of a detector to collimate an x-ray beam into smaller components. A fluence for each component is then measured by the detector and used to determine a total linear attenuation coefficient for all the voxels along the beams path (i.e., a voxel is a volume element, e.g., a 1×1×1 cm3 cube). If the beam is now rotated around an object, a reconstruction algorithm, e.g., filtered back projection, can be used to determine a linear attenuation coefficient for each individual voxel along the path. This information is then translated into Hounsfield units (HUs) that can be visually represented to create a CT scan. These HUs are then used to determine the electron density for each voxel, that can be used in dose calculations in radiation oncology. For the energy of interest to radiation oncology (~1 MeV–~20 MeV), a Compton effect is the dominant mechanism for scattering and attenuating photons. The Compton effect is independent of Z (the atomic number of an element or number of protons), since it assumes photon interactions only with free electrons. For most of the elements on the periodic table that occur in human tissue, the ratio of Z/A=½ is the same (except for hydrogen), i.e., the number of electrons/gram is approximately the same for these materials. A is the mass number of an element (number of nucleons). This means the electron density becomes independent of Z or A. Using the electron density, the amount of energy deposited in each voxel can be determined, which is essential for dose calculation in radiation oncology.

Figure 3:
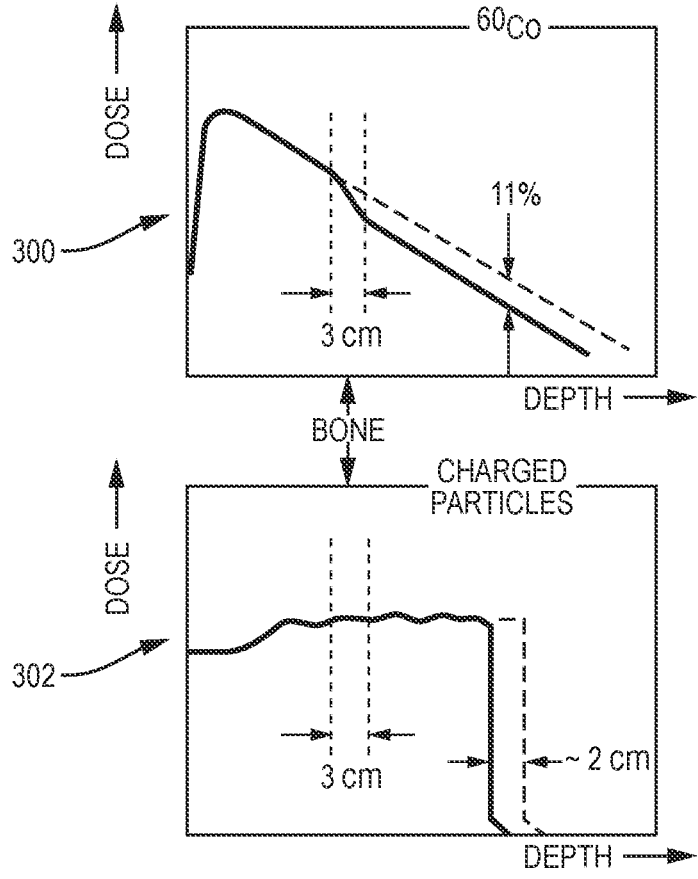
FIG. 3 illustrates a graph.

In FIG. 3, a top graph 300 illustrates that as photons traverse a body, its energy changes very little, but the number of photons in the beam decrease as the beam gets attenuated. The higher the density of an object, the more the beam gets attenuated. A bottom graph 302 illustrates as protons traverse an object, it continuously loses energy and thus the Bragg peak shifts relative to the density of the object and the material in the object.

Figure 4:
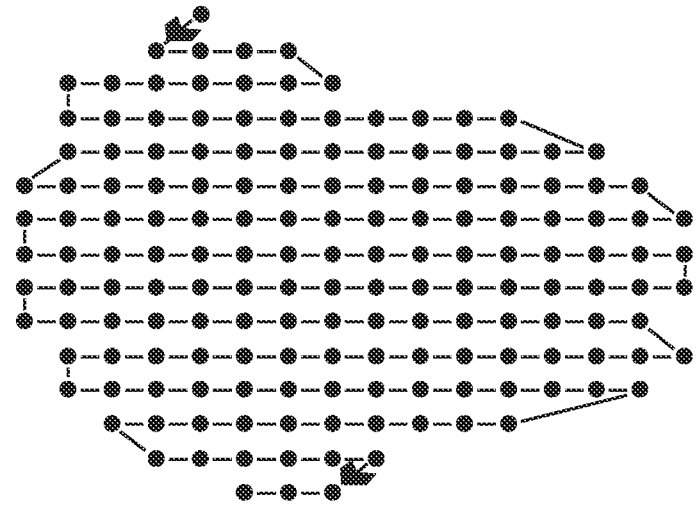
FIG. 4 illustrates painting a dose on a target.

In general, proton gantries are huge and accelerators are expensive. That has prohibited the clinical development of proton CT scanners in the past. One development that makes proton CT possible is the development of pencil beam scanning. In pencil beam scanning, a very thin beam of protons is scanned across an object and modulated in time to deposit a predetermined dose at specific positions, like "painting" the dose on the target (see FIG. 4). Previously, the field size was fixed and no adjustments where possible on the fly. Only by inserting new collimators.

To calculate dose deposited by protons, the mass stopping power(S) needs to be calculated from the energy loss per unit path length, as given below:

$$S/\rho = -\frac{1}{\rho}\frac{dE}{dx}\frac{Mev}{\text{g/cm}^2}$$

$$D = \frac{\text{energy}}{\text{mass}} = \frac{(dE/dx) \times \Delta x \times N}{\rho \times A \times \Delta x} = \Phi\frac{S}{\rho}$$

To calculate this dose accurately, knowledge of the material composition is essential, since the energy loss per unit path length is not independent of Z and A anymore, as can be seen from the Bethe-Bloch equation below, because the mean excitation potential (I) is dependent on Z. And protons interact with all the electrons in an atom, not just "free" electrons.

For a particle with speed v, change z and energy E traveling a distance x into a target of electron number density n and mean excitation potential l, $$-\frac{dE}{dx} = \frac{4\Pi}{m_e c^2} \cdot \frac{nz^2}{\beta^2} \cdot \frac{[c^2]^2}{[4\Pi\varepsilon_0]} \cdot \left[\ln\frac{[2m_e c^2 \beta^2]}{[I \cdot (1-\beta^2)]} - \beta^2\right]$$

where c is the speed of light and $\varepsilon_0$ the vacuum permittivity $\beta=\underline{v}$ e and me the electron charge and rest mass respectively.

Here, the electron density of the material can be calculated by $$n = \frac{N_A \cdot Z \cdot \rho}{A \cdot M_u}$$

where $\rho$ is the density of the material, Z its atomic number, A its relative atomic mass, $N_A$ the Avogadro number and $M_u$ the Molar mass constant.

With the advent of proton treatment in radiation oncology, the electron density is used to determine the stopping power of each voxel using photons. Currently x-ray CT scanners are used to develop treatment plans. Stopping powers for different materials are inferred from stoichiometric calculations for a number of tissues in humans to correct for errors that are introduced by using photons to determine electron densities. This led to a potential error in the dose calculation of ~2-5%. With a proton CT scanner, it is possible to calculate more accurate stopping powers for different tissues in the body, reducing the error in dose calculation. A proton CT scanner can also have uses as a diagnostic imaging tool, as well as reducing the radiation dose a patient receives during imaging, compared to that of an x-ray CT scanner. A proton CT scanner can be installed on existing proton gantries. There is also no need for beam collimation with pencil beam scanning.

Currently no commercially available device exists for acquiring proton CT scans. Devices that are used in research focus on measuring the Bragg peak position of a proton beam after exiting a subject to determine the energy lost in the beam's path. It uses an array of ion chambers to measure the dose to determine at what depth the Bragg peak occur. This information is used to determine the energy lost in the beam path as the beam traverse the patient.

Figures 5, 6, 7:
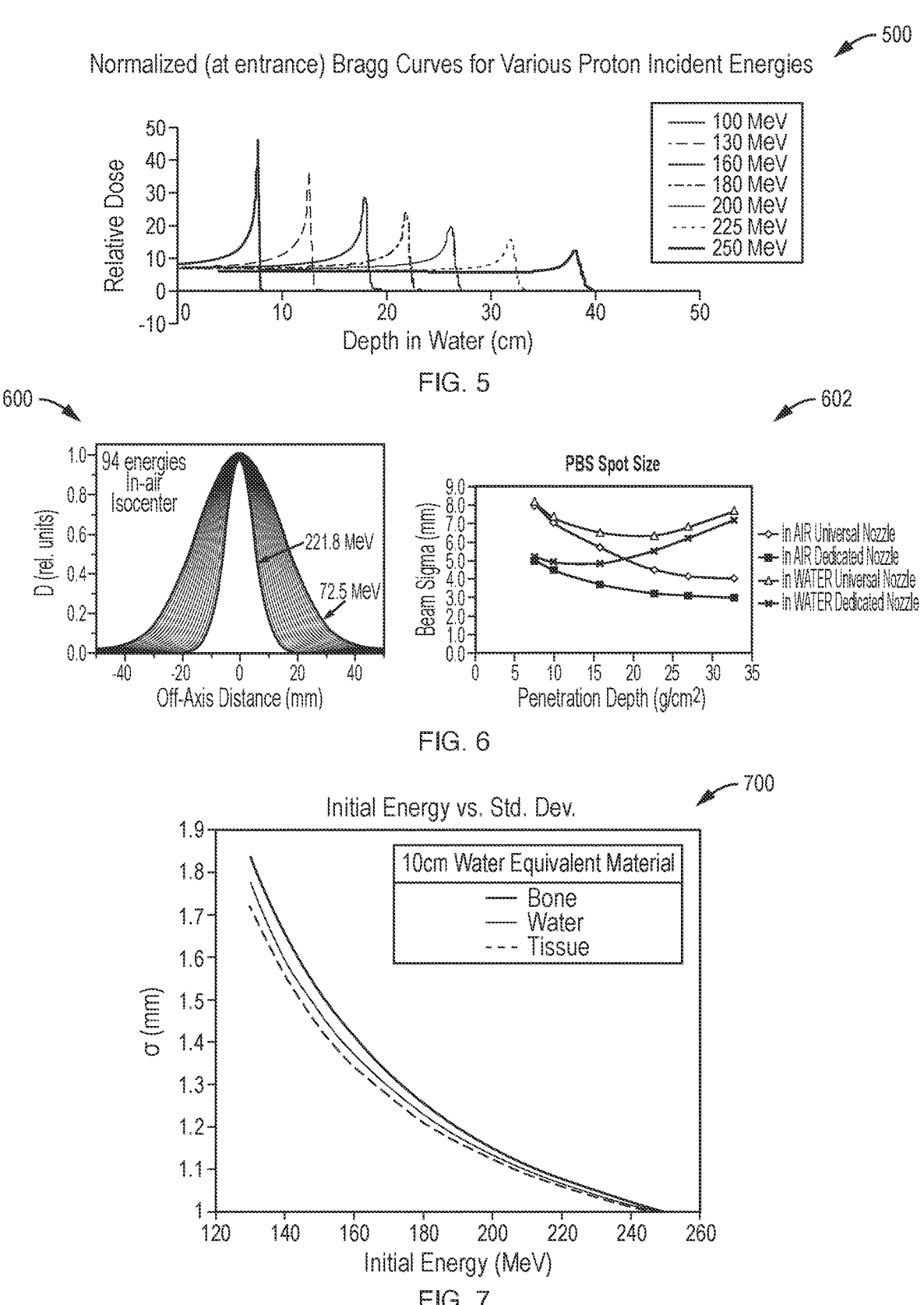
FIG. 5 illustrates a graph.
FIG. 6 illustrate graphs.
FIG. 7 illustrates a graph.

In FIG. 5, a graph 500 Bragg peaks for proton beams of different energy are illustrated. The entrance dose for protons is very low and most of its energy is deposited at the end of a protons track, creating the Bragg peak.

To measure the energy loss of a proton beam as it traverse a material, it needs to have enough energy to traverse the material. You also don't want unnecessary dose to be deposited inside the object by using an energy too low causing the Bragg peak to occur inside the object. Thus for proton CT, a proton beam energy of at least 250 MeV is necessary, resulting in a Bragg peak at a depth in water of ~39 cm. The object can also not be larger than 39 cm for an energy of 250 MeV, in order to be able to traverse an object and not stop inside the object. The exit energy can then be anything from 0-250 MeV, depending on the thickness and density of the object at each location of the beam. An ion chamber array must therefore be large enough to be able to measure any of these energies. These devices are typically expensive, large, and heavy, making it difficult to attach it to the gantry and rotate it around patients.

In FIG. 6, profiles for proton beams of different energies measured in air are illustrated in the graphs 600, 602. Note that the sigma becomes smaller as the energy increase in air. On the right (graph 602) it is shown that sigma will start to increase in water as function of energy as it traverses an object of different density and composition.

Protons also scatter during its trajectory through an object. This scatter depends on the electron density of the material, the mean ionization potential, and its thickness. This causes the scatter to vary for different energy beams and different materials. The amount of scatter can be measured by measuring the profile of the beam in air behind the object and determining the full width at half maximum of the Gaussian distribution. Full width at half maximum is proportional to a sigma value for the distribution. The profile can be measured in air by inserting a scintillator screen in the beam path and then reading it by optical means or by using an electronic portal imager.

The present invention uses two of the characteristics of the measured sigma value at the exit for a specific entrance beam energy:

(1) A correlation exist between the sigma and the exit energy of the beam, i.e., the total energy loss along beam path (thus thickness of object) can be determined by measuring sigma for a constant entrance energy. (Similar to measuring attenuation in a CT scanner). This dependence on energy can be seen in graph 600 in FIG. 6 and graph 700 in FIG. 7.

(2) The relation of sigma to total energy loss is different for a constant entrance energy if the beam traverse objects of different materials, but the same thickness. This is shown FIG. 7.

More specifically, in FIG. 7, the graph 700 illustrates that sigma measured at the exit as function of energy for different materials of the same mass thickness, i.e. 10 cm of water has an equivalent density as ~2 cm of bone if bone is 5 times denser than water. Note that sigma will be different if an equivalent mass thickness is traversed. Also for different energies (equivalent to different thickness of the same material) traversed, sigma change. This equivalent of keeping the entrance energy constant and traversing the beam through different thicknesses of the same material.

For a proton pencil beam of known energy entering an object, the sigma can be measured at the beam exit with a scintillator screen (as opposed to current methods using an array of ion chambers to measure the Bragg peak). By modeling sigma for proton beams traversing objects of different thickness and composition with a Monte Carlo model, correlations can be established with the exiting energy of the beam. By scanning the beam over the object in a plane and over 360 degrees around the object, then measuring the sigma of each pencil beam at the exit, the total energy loss for each beam path can be determined. This can be used to determine the relative stopping power in each voxel along the beams path and by using beams for all angles around the patient. By using multiple energies for separate scans, additional information can be extracted about each voxel, since the gradient of sigma vs energy is different for different entrance energies. Thus, even though two different materials may give the same relative stopping power for the same voxel, the composition can be more accurately determined by looking at the sigma values for a different entrance energy. All these observations are illustrated in FIG. 7. This process is similar to photon CT where the fluence is measured to determine total the linear attenuation coefficient. The beam energy must be high enough for a beam to have enough energy to traverse the object, this information can be acquired from the photon CT image or from the energy loss of the highest energy. By using the determined energy loss of each beam, a tomography image can be created using filtered backprojection or any method currently used in x-ray CT image reconstruction. A reconstruction will be done for each entrance energy used. These different energy images can be used to increase accuracy to resolve for Z and A in each voxel. This provides more accurate information for the relative stopping power in each voxel, which will improve dose calculation accuracy in radiation oncology. Lower energies can be used for thinner objects, to enhance the difference in energy loss for different materials as illustrated in FIG. 7 with a larger spread between sigma for the same energy, but different materials.

Since switching energy for protons repeatedly for each angle of acquisition might be challenging, a plastic wedge can be used, that can be opened and closed fast while keeping the energy from the cyclotron or synchrotron constant. Alternatively, all angles can be scanned with one energy, then the energy can be decreased and the scanning of all angles repeated.

Sigma can be measured by inserting a fluorescent screen in the beams path after it traversed the object. The light of the screen caused by proton interactions, can then be read either by a camera system (as illustrated in FIG. 2) or be using an electronic portal imaging device that reads it by using an array of photodiodes. Both of these devices are commercially available and are used routinely for quality insurance of proton therapy centers (See Lynx, IBA dosimetry or XRV-2000, Logos Systems, Scottsvalley, CA).

The methods of the present invention can be used for any charge particle CT image reconstruction, e.g., protons, carbon ions, helium ions.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed is:

1. A method of proton computed tomography, comprising:
providing a proton computed tomography (CT) scanner;
configured to deliver a scanning proton pencil beam and
   to rotate relative to an object;
for a proton pencil beam of a first known entrance energy,
   scanning the pencil beam over the object at a plurality
   of gantry angles and, for each pencil-beam position of
   a scan pattern at each gantry angle, measuring on a
   fluorescent scintillator screen located in air down-
   stream of the object a one-dimensional intensity profile
   of an exit proton beam by acquiring, with an optical
   camera or an electronic portal imaging device of a type
   used for quality assurance of proton therapy beams, an
   image of the scintillator screen and determining a
   beam-width parameter $\sigma\_exit$ from a Gaussian fit to the
   one-dimensional intensity profile, wherein $\sigma\_exit$ is
   computed from a full width at half maximum (FWHM)
   of the fit;
using a Monte Carlo model of proton transport to gener-
   ate, for the first entrance energy, a correlation between
   $\sigma\_exit$ and residual beam energy for proton beams
   traversing objects of different thickness and composi-
   tion and, for each respective pencil-beam path, deter-
   mining a total energy loss along the path by a applying
   the correlation to the measured $\sigma\_exit$ for that path;
reconstructing, from the total-energy-loss values for the
   pencil-beam paths, a first three-dimensional map of
   relative stopping power of the object corresponding to
   the first entrance energy;
repeating the scanning, measuring, determining and
   reconstructing steps for at least a second entrance
   proton energy different from the first entrance energy to
   obtain a second three-dimensional map of relative
   stopping power of the object; and
comparing the first and second three-dimensional maps of
   relative stopping power to determine, for voxels of the
   object, information about material composition based
   on a dependence of $\sigma\_exit$ on entrance energy;
wherein the method determines the total energy loss
   without measuring a Bragg-peak depth using an ion-
   chamber array.

2. The method of claim 1, wherein, for a constant entrance energy, σ_exit depends on the composition and thickness of the material traversed along a beam path.

3. The method of claim 2, further comprising:

performing the measuring of the one-dimensional intensity profile recited in claim 1 at a plurality of entrance energies by conducting separate scans for each pencil-beam path, and, for each beam path, using the variation of σ_exit with entrance energy to obtain additional information about the material along the path.

4. A method comprising:

providing a proton computed tomography (CT) scanner; configured to deliver a scanning proton pencil beam and to rotate relative to an object;

for a proton pencil beam of a first known entrance energy entering the object, inserting a fluorescent scintillator screen in air downstream of the object and acquiring a beam profile of an exit proton beam by recording, with an optical camera or an electronic portal imaging device of a type used for quality assurance of proton therapy beams, an image of the fluorescent scintillator screen, and determining a sigma (σ_exit) for the exit beam by determining a full width at half maximum (FWHM) of a Gaussian distribution of a one-dimensional intensity profile of the beam recorded on the image;

using a Monte Carlo model of proton transport to generate, for the first entrance energy, a correlation between σ_exit and exiting energy of the beam for proton beams traversing objects of different thickness and composition;

scanning the pencil beam over the object in a plane and over 360 degrees around the object, using the fluorescent scintillator screen and the optical camera or electronic portal imaging device to measure σ_exit of each pencil beam at the exit, and determining a total energy loss for each beam path from the correlation;

repeating the scanning, measuring, and determining steps for at least a second entrance energy different from the first entrance energy so as to obtain, for each beam path, σ_exit values as a function of entrance energy; and using differences in a dependence of σ_exit on entrance energy to determine, for voxels along the beam paths, information about material composition including atomic number and mass number;

wherein determining the total energy loss is performed without measuring a Bragg-peak depth using an ion-chamber array.

5. The method of claim 4 further comprising:

determining a relative stopping power in each voxel along the beam path.

6. The method of claim 4, further comprising:

reconstructing, from the total energy losses determined for the pencil-beam paths, a three-dimensional map of relative stopping power of the object to obtain a relative stopping power value for each voxel.

* * * * *